US009677111B2

(12) United States Patent
Binsfeld et al.

(10) Patent No.: US 9,677,111 B2
(45) Date of Patent: *Jun. 13, 2017

(54) **METHOD OF DETECTING A *SALMONELLA* MICROORGANISM**

(71) Applicant: 3M INNOVATIVE PROPERTIES COMPANY, St. Paul, MN (US)

(72) Inventors: Chirstine A. Binsfeld, Woodbury, MN (US); Patrick A. Mach, Shorewood, MN (US); Mara S. Celt, Red Wing, MN (US); Adam J. Stanenas, Cottage Grove, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 188 days.

This patent is subject to a terminal disclaimer.

(21) Appl. No.: 14/368,525

(22) PCT Filed: Dec. 18, 2012

(86) PCT No.: PCT/US2012/070223
§ 371 (c)(1),
(2) Date: Jun. 25, 2014

(87) PCT Pub. No.: WO2013/101530
PCT Pub. Date: Jul. 4, 2013

(65) Prior Publication Data
US 2014/0356888 A1 Dec. 4, 2014

Related U.S. Application Data

(60) Provisional application No. 61/580,860, filed on Dec. 28, 2011.

(51) Int. Cl.
*C12Q 1/10* (2006.01)
*C12Q 1/34* (2006.01)
*C12Q 1/04* (2006.01)

(52) U.S. Cl.
CPC ............. *C12Q 1/34* (2013.01); *C12Q 1/04* (2013.01); *C12Q 2304/00* (2013.01); *C12Q 2334/00* (2013.01)

(58) Field of Classification Search
USPC ... 435/34, 30, 18, 21, 243, 253.6, 39, 4, 38; 424/283.1; 514/81
IPC ........ A61K 31/685,31/522, 47/48; C12Q 1/10, 1/34
See application file for complete search history.

(56) References Cited

U.S. PATENT DOCUMENTS

| 4,565,783 A | 1/1986 | Hansen et al. |
| 5,601,998 A | 2/1997 | Mach et al. |
| 5,681,712 A | 10/1997 | Nelson |
| 5,726,031 A | 3/1998 | Roth et al. |
| 5,786,167 A | 7/1998 | Tuompo et al. |
| 5,871,944 A | 2/1999 | Miller et al. |
| 6,022,682 A | 2/2000 | Mach et al. |
| 6,243,486 B1 | 6/2001 | Weiss |
| 6,265,203 B1 | 7/2001 | Ushiyama |
| 6,638,755 B1 | 10/2003 | Mizuochi et al. |
| 7,150,977 B2 | 12/2006 | Restaino |
| 7,351,574 B2 | 4/2008 | Vent |
| 7,496,225 B2 | 2/2009 | Graessle et al. |
| 2003/0170773 A1 | 9/2003 | Tsoraeva et al. |
| 2004/0029212 A1 | 2/2004 | Rodriguez Martinez et al. |
| 2013/0273598 A1* | 10/2013 | Moriyama ............... C12Q 1/04 435/38 |

FOREIGN PATENT DOCUMENTS

| JP | 2004-501654 | 1/2004 |
| WO | WO 96/30543 | 10/1996 |
| WO | WO 98/55644 | 12/1998 |
| WO | WO 2007/017601 | 2/2007 |
| WO | WO 2010/079025 | 7/2010 |
| WO | WO 2012/092181 | 7/2012 |
| WO | WO 2012/161992 | 11/2012 |
| WO | WO 2013/101590 | 7/2013 |

OTHER PUBLICATIONS

Jameson. 1962. A discussion of the dynamics of *Salmonella* enrichment. Journal of Hygiene, Cambridge, vol. 60, p. 193-207.*
Nabbut.1973. Elevated temperature technique for the isolation of *Salmonellas* from sewage and human faces Journal of Hygiene, vol. 71, pp. 49-54.*
Bulmash, J. et al.; "Lactose and Sulfide Reactions of an Aberrant *Salmonella* Strain"; Journal of Bacteriology; vol. 89, No. 1; 1965; p. 259.
Chevalier, P. et al.; "X-α-Gal-based medium for simultaneous enumeration of bifidobacteria and lactic acid bacteria in milk"; Journal of Microbiological Methods; vol. 13; 1991; pp. 75-83.
Fookes, M. et al.; "*Salmonella bongori* Provides Insights into the Evolution of the *Salmonellai*"; PLOS Pathogens; vol. 7, No. 8; 2011; e1002191 (16 pgs).
Gonzalez, A.; "Lactose-Fermenting *Salmonella*"; Journal of Bacteriology; vol. 91, No. 4; 1966; pp. 1661-1662.
Littell, A.; "Plating Medium for Differentiating *Salmonella arizonae* from Other Salmonellae"; Applied and Environmental Microbiology; vol. 33, No. 2; 1977; pp. 485-487.

(Continued)

*Primary Examiner* — Debbie K Ware
*Assistant Examiner* — Kailash C Srivastava
(74) *Attorney, Agent, or Firm* — 3M Innovative Properties Company; Michael G. Williams

(57) ABSTRACT

A method of detecting a *Salmonella* microorganism is provided. The method includes the use of a selective growth medium, a first indicator system that is converted to a first detectable product by a *Salmonella* microorganism, and a second indicator system that is converted to a second detectable product by β-galactosidase enzyme activity. The method further comprises inoculating the growth medium and incubating the inoculated growth medium at a temperature higher than 40 degrees C.

26 Claims, 2 Drawing Sheets

(56) References Cited

OTHER PUBLICATIONS

Manafi, M.; New developments in chromogenic and fluorogenic culture media:; International Journal of Food Microbiology; vol. 60; 2000; pp. 205-218 (XP-002177549).
Matsen, J. et al.; "Characterization of Indole-Positive *Proteus mirabilis*"; Applied Microbiology; vol. 23, No. 3; 1972; pp. 592-594.
Perry, J. et al.; "ABC Medium, a New Chromogenic Agar for Selective Isolation of *Salmonella* spp."; Journal of Clinical Microbiology; vol. 37, No. 3; 1999; pp. 766-768 (XP-002154638).
Rambach, A.; "New Plate Medium for Facilitated Differentiation of *Salmonella* spp. from *Proteus* spp. and Other Enteric Bacteria"; Applied and Environmental Microbiology; vol. 56, No. 1; 1990; pp. 301-303.
Presentation by Ana Paccagnella entitled "Naming the *Salmonellae*: all you wanted to know about Saintpaul, Sandiego, Heidelberg. Muenchen and other destinations"; 2005; 36 pgs.
Brochure entitled "Interpretation Guide—3M Petrifilm™ Enterobacteriaceae Count Plate"; from 3M Food Safety; 2010; No. 70-2008-8668-0 (90.2)ii (6 pgs).
Brochure entitled "Urea Agar Base (7226)"; from NEOGEN Corporation; 2010; No. PI 7226, Rev. 4; (3 pgs).

\* cited by examiner

METHOD OF DETECTING A *SALMONELLA* MICROORGANISM

CROSS REFERENCE TO RELATED APPLICATIONS

This application is a national stage filing under 35 U.S.C. 371 of PCT/US2012/070223, filed Dec. 18, 2012, which claims priority to U.S. Provisional Patent Application No. 61/580,860, filed Dec. 28, 2011, which is incorporated by reference in its entirety herein.

BACKGROUND

The family Enterobacteriaceae includes a large number of metabolically-diverse, facultatively-anaerobic bacteria that are capable of fermenting sugars to lactic acid and other end products. The family includes several well-known human pathogens such as *Escherichia coli*, several subspecies of *Salmonella*, *Yersinia pestis*, several species of *Klebsiella*, and several species of *Shigella*.

The genus *Salmonella* includes two species, *S. enterica* and *S. bongori*, that include subspecies capable of causing illness in humans. Some of the pathogenic Salmonellae can be transmitted to humans via the ingestion of contaminated food or beverages. The detection of *Salmonella* microorganisms in food samples can be difficult due to the presence of relatively low numbers of the *Salmonella* microorganisms in the sample, the presence of relatively high numbers of closely-related non-*Salmonella* enteric microorganisms in the sample, and/or the presence of non-microorganism materials (e.g., food particles or soluble chemicals) in the sample that can interfere with the growth or detection of the *Salmonella* microorganisms.

A variety of selective and/or differential microbiological culture media have been developed to detect *Salmonella* microorganisms in a sample and to distinguish them from one or more non-*Salmonella* microorganisms. Typically, these culture media include a selective agent that inhibits the growth of non-enteric microorganisms. In addition, many of these culture media rely on one or more differential indicator systems to distinguish between *Salmonella* and non-*Salmonella* microorganisms.

In spite of the variety of microbiological culture media to detect *Salmonella* microorganisms in a sample, there remains a need for improved methods to detect a *Salmonella* microorganism in a sample.

SUMMARY

In general, the present disclosure relates to a method of detecting a *Salmonella* microorganism. In particular the method includes the use of a selective growth medium that includes a positive differential indicator system (i.e., an indicator system that includes an indicator compound that is converted to a detectable product by a *Salmonella* microorganism) and a negative differential indicator system (i.e., an indicator system that includes an indicator compound that can be converted to a detectable product by a β-galactosidase enzyme activity and, thus, is not converted to a detectable product by a *Salmonella* microorganism). Surprisingly, members of the *S. bongori* species do not react with the second indicator system at incubation temperatures above 40 degrees C.

In one aspect, the present disclosure provides a method of detecting a *Salmonella* microorganism. The method can comprise providing a sample to be tested, a culture device, a nutrient medium that facilitates growth of a Gram-negative enteric microorganism, a first selective agent that inhibits the growth of Gram-positive microorganisms, a first differential indicator system comprising a first differential indicator compound that can be converted to a first detectable product by a member of a group of *Salmonella* microorganisms that includes a microorganism of the species *Salmonella bongori*, and a second differential indicator system comprising a second differential indicator compound that can be converted to a second detectable product by a β-galactosidase enzyme activity. The method further can comprise contacting in the culture device the nutrient medium, the first selective agent, the first differential indicator system, and the second differential indicator system with a sample to form an inoculated culture device, incubating the inoculated culture device for a first period of time at a temperature greater than 40 degrees C., observing the culture device to detect a presence or an absence of the first detectable product, and observing the culture device to detect a presence or an absence of the second detectable product; wherein observing the presence of the first detectable product indicates a possible presence in the sample of a *Salmonella* microorganism; wherein observing the presence of the first detectable product juxtaposed with the second detectable product indicates a presence in the sample of a microorganism other than a β-galactosidase-producing member of the species *Salmonella bongori*.

In any embodiment, the culture device can be provided as a thin film culture device with the nutrient medium, the first selective agent, the first differential indicator system, and the second differential indicator system disposed therein in a substantially dehydrated form. In any of the above embodiments, observing the absence of the first detectable product can indicate an absence of a *Salmonella* microorganism in the sample. In any of the above embodiments, observing the nutrient medium to detect the presence of the first detectable product can comprise observing the culture device to detect a first detectable color. In any of the above embodiments, the first differential indicator compound can comprise an enzyme substrate. In some embodiments, the enzyme substrate can comprise an enzyme substrate to detect caprylate esterase enzyme activity or to detect α-galactosidase enzyme activity. In some embodiments, the enzyme substrate can be selected from the group consisting of 5-bromo-6-chloro-3-indolyl caprylate, 4-nitrophenyl caprylate, 2-naphthyl caprylate, 5-bromo-4-chloro-3-indoxyl-α-D-galactopyranoside, resorufinyl-α-D-galactopyranoside, and 4-nitrophenyl-α-D-galactopyranoside.

In any of the above embodiments, the first differential indicator system can comprise a pH indicator and at least one carbohydrate selected from the group consisting of melibiose, 2-deoxy-D-ribose, mannitol, L-arabinose, dulcitol, maltose, L-rhamnose, trehalose, D-xylose, and sorbitol.

In any of the above embodiments, the first detectable product can be substantially water-soluble, wherein observing the first detectable product can comprise observing a colored zone adjacent a microbial colony.

In any of the above embodiments, observing the second detectable product comprises observing the culture device to detect a second detectable color. In any of the above embodiments, the second differential indicator compound can be selected from the group consisting of 5-bromo-4-chloro-3-indolyl-β-D-galactopyranoside, 5-bromo-3-indolyl-β-D-galactopyranoside, 5-bromo-6-chloro-3-indolyl-β-D-galactopyranoside, 2-nitrophenyl-β-D-galactopyranoside, and 4-nitrophenyl-β-D-galactopyranoside.

In any of the above embodiments, the first detectable product can be substantially water-soluble and the second detectable produce can be substantially water-insoluble or, alternatively, wherein the first detectable product can be substantially water-insoluble and the second detectable produce can be substantially water-soluble.

In any of the above embodiments, the first selective agent is selected from the group consisting of an antibiotic, bile salts, bile salts No. 3, deoxycholic acid, cholic acid, deoxycholic acid, crystal violet, novobiocin, nalidixic acid, polymyxin B, streptomycin, methicillin, cefsoludin, or a combination of any two or more of the foregoing selective agents. In any of the above embodiments, the culture device further can comprise at least one second selective agent, wherein the at least one second selective agent inhibits the growth of at least one Gram-negative enteric microorganism that is not a member of the genus Salmonella. In some embodiments, the second selective agent can be selected from the group consisting of a β-lactam antibiotic, an aminoglycoside antibiotic, a quinolone antibiotic, a sulfa antibiotic, a polymyxin antibiotic, and a combination of any two or more of the foregoing antibiotics. In some embodiments, the at least one second selective agent comprises a combination of naladixic acid, streptomycin, and polymyxin B. In any of the above embodiments, incubating the culture device comprises incubating the culture device at a temperature between 41-44 degrees C., inclusive.

In any of the above embodiments, the method further can comprise providing an article with a third differential indicator system comprising a third differential indicator compound that can be converted by a Salmonella microorganism to a third detectable product, contacting the article with the inoculated culture device, incubating the inoculated culture device for a second period of time, and observing the culture device to detect the third detectable product; observing the third detectable product juxtaposed with the first detectable product indicates the presence of a Salmonella microorganism in the sample.

In any of the above embodiments, the method further can comprise providing a nondifferential indicator compound that can be converted by an enteric microorganism to a fourth detectable product and observing the culture device to detect a presence or an absence of the fourth detectable product; wherein contacting in the culture device the nutrient medium, the first selective agent, the first differential indicator system, and the second differential indicator system with a sample to form an inoculated culture device further comprises contacting in the culture device the nutrient medium, the first selective agent, the first differential indicator system, the second differential indicator system, and the nondifferential indicator compound with the sample to form the inoculated culture device.

In any of the above embodiments, observing the culture device can comprise observing the culture device visually. In any of the above embodiments, observing the culture device can comprise creating an image of the culture device using an imaging device. In any of the above embodiments, the method further can comprise analyzing the image using a processor. In any of the above embodiments, the method further can comprise enumerating a number of colonies formed by a microorganism belonging to the group.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

"Salmonella microorganism", as used herein, refers to any microorganism belonging to the genus Salmonella.

"Differential indicator system", as used herein, refers to one or more compounds that are used to distinguish two types of microorganisms based upon their respective ability to convert a differential indicator compound to a detectable product. In some instances, for example, the differential indicator compound (e.g., 2-nitrophenyl-β-D-galactoside) may be converted by a type of microorganism directly to the detectable product (e.g., 2-nitrophenol). In some instances, for example, the differential indicator compound (e.g., 5-bromo-4-chloro-3-indoxyl-α-D-galactopyranoside) may be converted by a type of microorganism to an intermediate product that, in the presence of air can react to form the detectable product (a type of indigo dye). In some instances, for example, the differential indicator compound (e.g., a fermentable carbohydrate such as melibiose) can be converted by a type of microorganism to the detectable product (e.g., lactic acid), which can react with another component of the differential indicator system (e.g., a pH indicator such as chlorophenol red) to cause a detectable color change in the other component.

"Selective agent", as used herein, refers to a chemical compound that inhibits the growth of first microorganism or a first group of microorganisms to a greater degree than a second microorganism or a second group of microorganisms, thereby favoring the growth of the less-inhibited microorganism(s).

The terms "comprises" and variations thereof do not have a limiting meaning where these terms appear in the description and claims.

As used herein, "a," "an," "the," "at least one," and "one or more" are used interchangeably. Thus, for example, a microorganism can be interpreted to mean "one or more" microorganisms.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Additional details of these and other embodiments are set forth in the accompanying drawings and the description below. Other features, objects and advantages will become apparent from the description and drawings, and from the claims.

DETAILED DESCRIPTION

Figure 1:
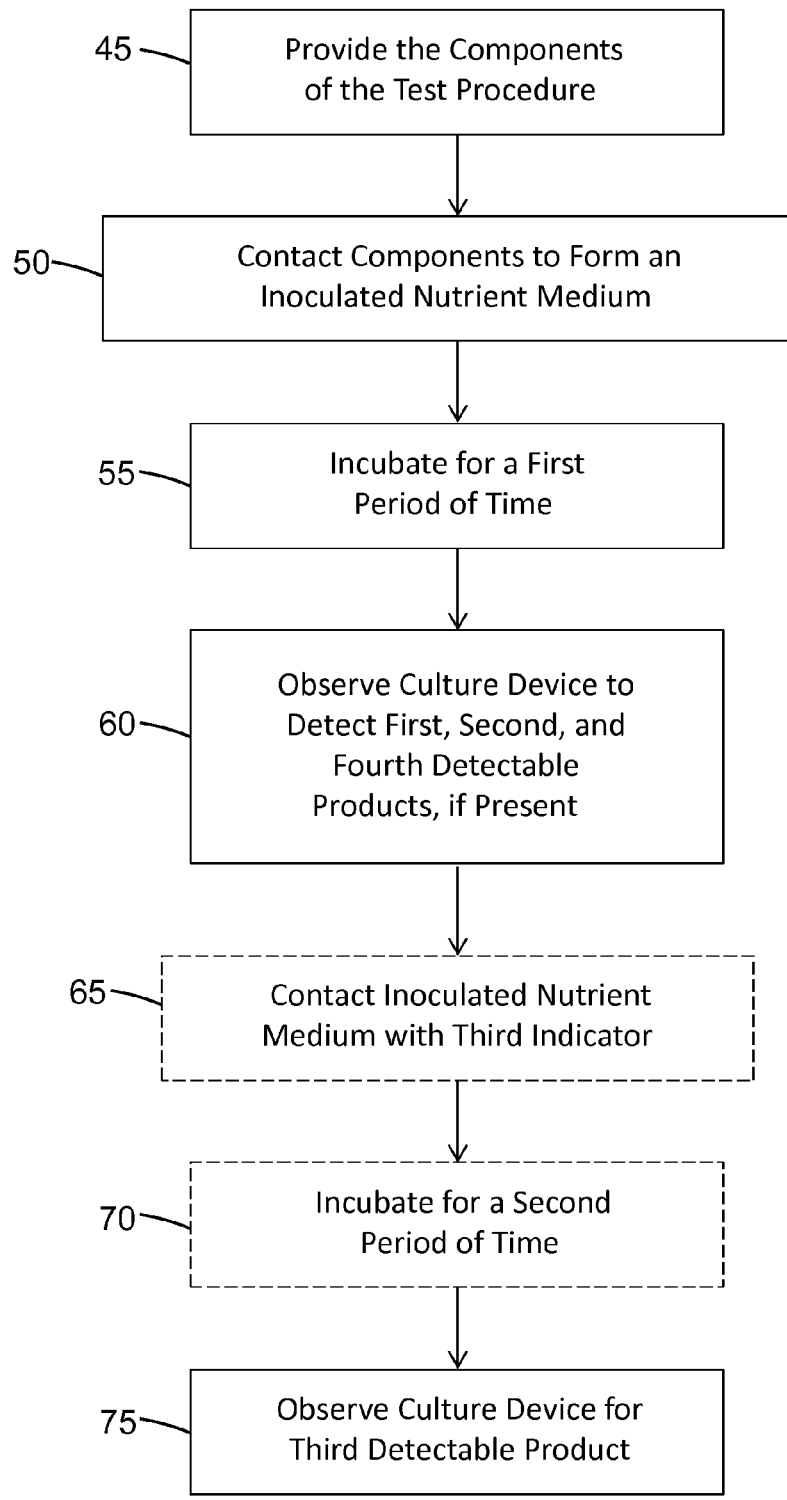
FIG. 1 shows a block diagram of one embodiment of a method of detecting a Salmonella microorganism according to the present disclosure.

The genus *Salmonella* includes two species, *Salmonella enterica* and *Salmonella bongori*. The genetic relatedness of the two species has been studied by Fookes et al. ("*Salmonella bongori* Provides Insights into the Evolution of the Salmonellae", PLOs Pathogens at www.plospathogens.org, 2011, vol. 7, article number e1002191, p 1-16, which is incorporated herein by reference in its entirety). Although subspecies of *S. enterica* are better known than *S. bongori* for their ability to infect and cause disease in humans, *S. bongori* has also been shown to cause human infections. Thus, a test designed to detect potentially-pathogenic *Salmonella* microorganisms should be capable of detecting both species.

The present disclosure generally relates to a method for detecting *Salmonella* microorganisms in a sample. In particular, the present disclosure relates to a growth-based detection method that is capable of distinguishing certain β-galactosidase-producing *Salmonella* microorganisms (e.g., members of the species *S. bongori*) from β-galactosidase-producing non-*Salmonella* microorganisms (e.g., *Escherichia coli* and other β-galactosidase-producing members of the Enterobacteriaceae family). The inventive method combines a selective growth medium that includes a plurality of differential indicator reagents with an elevated incubation temperature to differentiate *S. bongori* microorganisms.

Growth-based detection and identification of *Salmonella* generally requires the use of biochemical reactions that specifically detect *Salmonella* strains in the presence of non-*Salmonella* microorganisms. Unfortunately, most of the conventional detection systems do not provide for adequate specificity to differentiate *Salmonella* microorganisms from non-*Salmonella* Enterobacteriaceae microorganisms that may be present in the sample. The tests often require additional reagents and procedures (e.g., immunological or genetic tests) to differentiate non-*Salmonella* microorganisms from *Salmonella* microorganisms found in a sample.

Unfortunately, some of the reactions that are commonly used to detect groups of non-*Salmonella* enteric microorganisms (e.g. coliform bacteria) do not negatively-differentiate all *Salmonella* strains. For example, there are some *Salmonella* strains that are lac positive (produce β-D-galactosidase) and, thus, are not negatively-differentiated from non-*Salmonella* microorganisms in tests that use β-galactosidase enzyme substrates (e.g., 5-bromo-4-chloro-3-indolyl-β-D-galactopyranoside). The investigators have discovered that certain β-D-galactosidase-positive *Salmonella* strains do not react with the β-galactosidase enzyme substrates when incubated at elevated temperatures. In addition, the elevated incubation temperature can inhibit the growth of some non-*Salmonella* β-galactosidase-producing microorganisms and/or does not substantially affect the ability to detect their β-galactosidase enzyme activity. Thus, the present disclosure provides a method for the differentiation of growing colonies of *Salmonella bongori* from colonies of other β-galactosidase-producing enteric microorganisms.

The present disclosure provides a method of detecting a *Salmonella* microorganism in a sample. FIG. 1 shows one embodiment of a method 10 of detecting a *Salmonella* microorganism in a sample.

The method 10 comprises the step 45 of providing the components of the test procedure. Providing the components of the test procedure includes providing a sample to be tested, a culture device, a nutrient medium that facilitates growth of a Gram-negative enteric microorganism; a first selective agent that inhibits the growth of Gram-positive microorganisms, a first differential indicator system comprising a first differential indicator compound that can be converted to a first detectable product by a member of a group of *Salmonella* microorganisms that includes a microorganism of the species *Salmonella bongori*, and a second differential indicator system comprising a second differential indicator compound that can be converted to a second detectable product by a β-galactosidase enzyme activity. The method 10 further comprises the step 50 of contacting the components of the test procedure to form an inoculated nutrient medium. Contacting the components of the test procedure to form an inoculated nutrient medium includes contacting; in the culture device; the nutrient medium, the selective agent, the first differential indicator system, and the second differential indicator system with the sample to form an inoculated culture medium. The method 10 further comprises the step 55 of incubating the inoculated culture medium for a first period of time at a temperature greater than 40 degrees C. and the step 60 of observing the culture device to detect a presence or absence of the first detectable product and observing the culture device to detect a presence or an absence of the second detectable product. In these embodiments, observing the presence of the first detectable product indicates a possible presence in the sample of a *Salmonella* microorganism (e.g., *Salmonella enterica* and/or *Salmonella bongori*). Observing the presence of the first detectable product juxtaposed with the second detectable product indicates a presence in the sample of a microorganism other than a β-galactosidase-producing member of the species *Salmonella bongori*.

In some embodiments, the method 10 further can comprise the optional step 65 of contacting the inoculated nutrient medium with a third differential indicator system comprising a third differential indicator compound that can be converted by a *Salmonella* microorganism to a third detectable product, as described herein.

The third differential indicator system can be contacted with the inoculated nutrient medium using a variety of procedures, including those described herein for contacting the first differential indicator compound, second differential indicator compound, third differential indicator compound, or the nondifferential indicator compound with the sample and/or nutrient medium. In addition, the third differential indicator system can be contacted with the inoculated nutrient medium after the first incubation period by contacting an article comprising the third indicator system with the inoculated nutrient medium. This may be performed, for example, by using an article having a coating comprising the third differential indicator system. For example, the article may comprise a coating and/or a coated substrate as described in U.S. Pat. No. 6,022,682; which is incorporated herein by reference in its entirety.

After the third differential indicator system comprising a third differential indicator compound is contacted with the inoculated nutrient medium, the method may include the optional step 70 of incubating the plate for a second period of time. During the second period of incubation, a *Salmonella* microorganism, if present, may convert the third differential indicator compound to a third detectable product.

In some embodiments, the method 10 can further comprise the optional step (not shown) of providing a nondifferential indicator compound. In these embodiments, contacting; in the culture device; the sample, the nutrient medium, the first selective agent, the first differential indicator system, and the second differential indicator system to form an inoculated culture medium optionally may further comprise contacting; in the culture device, the sample, the nutrient medium, the first selective agent, the first differential indicator system, the second differential indicator system with a nondifferential indicator compound to form the inoculated culture medium. The nondifferential indicator compound can be contacted with the other components of the inoculated culture medium using any suitable method including those described herein.

Suitable nondifferential indicator compounds include indicator compounds that are metabolized by, or otherwise react with, growing microorganisms, and in doing so to produce a fourth detectable product which may cause the microbial colonies or the nutrient medium adjacent the colonies to be colored or fluoresce for ease of visualization, imaging, and/or quantitation. The nondifferential indicator, and the fourth detectable product derived therefrom, should not substantially interfere with the detection of the first detectable product or the second detectable product and/or the third detectable product, if present in the inoculated culture medium. Nonlimiting examples of suitable nondifferential indicator compounds include chromogenic redox indicators such as triphenyl tetrazolium chloride, p-tolyl tetrazolium red, tetrazolium violet, veratryl tetrazolium blue, and 5-bromo-4-chloro-3-indolyl-phosphate disodium salt. In an embodiment where a nondifferential indicator is contacted with the inoculated nutrient medium, observing the culture device to detect the presence of the first and/or second detectable product may further comprise observing the culture device to detect a presence of the fourth detectable product.

Samples tested in the method of the present disclosure include a variety of samples that may be suspected of containing a *Salmonella* microorganism. Samples of particular interest include raw material, in-process material, or finished product material from food-processing or beverage-processing operations. Other suitable samples include, for example, water samples (e.g., surface water, process water), environmental samples (e.g., air samples; surface samples from walls, floors, drains, food-contact surfaces, process equipment); and clinical samples). Non-limiting examples of clinical samples include gastrointestinal samples, rectal samples, and fecal samples. Test samples may include liquids, as well as solid(s) dissolved or suspended in a liquid medium.

Culture devices of the present disclosure include any culture device that is used to hold a nutrient medium in a process to detect microorganisms present in a sample. In certain preferred embodiments, the nutrient medium comprises a gelling agent to facilitate enumeration of the microorganisms. Nonlimiting examples of suitable culture devices include Petri dishes, multi-well plates, tubes, flasks, thin film culture devices (e.g., the thin film culture devices disclosed in U.S. Pat. Nos. 4,565,783; 5,601,998; 5,681,712; 6,265,203; and 6,638,755; each of which is incorporated herein by reference in its entirety), and the like.

In some embodiments, providing a culture device may comprise providing a culture device that contains a nutrient medium that facilitates growth of a Gram-negative enteric microorganism, a first selective agent that inhibits the growth of Gram-positive microorganisms, a first differential indicator system comprising a first differential indicator compound that can be converted to a first detectable product by a member of a group of *Salmonella* microorganisms that includes a microorganism of the species *Salmonella bongori*, and/or a second differential indicator system comprising a second differential indicator compound that can be converted to a second detectable product by a β-galactosidase enzyme activity.

In some embodiments, at least one component selected from the nutrient medium that facilitates growth of a Gram-negative enteric microorganism; the first selective agent that inhibits the growth of Gram-positive microorganisms; the first differential indicator system comprising a first differential indicator compound that can be converted to a first detectable product by a member of a group of *Salmonella* microorganisms that includes a microorganism of the species *Salmonella bongori*; and/or the second differential indicator system comprising a second differential indicator compound that can be converted to a second detectable product by a β-galactosidase enzyme activity is provided (optionally, in the culture device) in a substantially dehydrated state. In these embodiments, the at least one dehydrated component can be rehydrated with an aqueous liquid (e.g., water, a buffer solution, a diluent, a liquid sample) before or during contact with the sample.

In some embodiments, at least one component selected from the nutrient medium that facilitates growth of a Gram-negative enteric microorganism; the first selective agent that inhibits the growth of Gram-positive microorganisms; the first differential indicator system comprising a first differential indicator compound that can be converted to a first detectable product by a member of a group of *Salmonella* microorganisms that includes a microorganism of the species *Salmonella bongori*; and/or the second differential indicator system comprising a second differential indicator compound that can be converted to a second detectable product by a β-galactosidase enzyme activity is mixed with the sample (e.g., dissolved or diluted in a liquid sample) prior to adding the component to the culture device.

Nutrient media of the present disclosure include any nutrient medium that facilitates growth of a Gram-negative enteric microorganism. A variety of suitable nutrient media are known in the art. Suitable nutrient media include proteinaceous nutrients (e.g., chemical and/or enzymatic digests of animal or vegetable proteins), which can provide carbon, nitrogen, and energy to facilitate the growth of Gram-negative enteric microorganisms. The nutrient medium may comprise other nutrients (e.g. minerals or other components), provided they do not substantially interfere with the function of first differential indicator system, the second differential indicator system, and/or the third differential indicator system, if present.

The first differential indicator system of the present disclosure comprises a first differential indicator compound that can be converted to a first detectable product by a *Salmonella* microorganism. Preferably, the first differential indicator compound can be converted to the first detectable product by a member of a group of *Salmonella* microorganisms that includes a microorganism of the species *Salmonella bongori*. More preferably, the first differential indicator compound also is converted to the first detectable product by a *Salmonella* microorganism belonging to a species other than *S. bongori* (e.g., *S. enterica*). In some embodiments, the first differential indicator system comprises a first differential indicator compound that can be converted to a first detectable product by at least one non-*Salmonella* enteric microorganism capable of growing in the culture device.

In some embodiments, the first differential indicator compound is a nutrient compound (e.g., a carbohydrate) that can be converted (e.g., via fermentation) by a *Salmonella* microorganism to a first detectable product (e.g., an acidic compound such as lactic acid, for example, and/or a gas such as carbon dioxide, for example). Preferably, the first differential indicator comprises a nutrient compound that is converted to the first detectable product by a plurality of *Salmonella* species and/or subspecies to the first detectable product. More preferably, the first differential indicator comprises a nutrient compound that is not converted to the first detectable product by many species of microorganisms that do not belong to the genus *Salmonella*. Even more preferably, the first differential indicator comprises a nutrient compound that is not converted to the first detectable product by a non-*Salmonella* microorganism. Non-limiting examples of suitable first differential indicators include a compound selected from the group consisting of melibiose, 2-deoxy-D-ribose, mannitol, L-arabinose, dulcitol, maltose, L-rhamnose, trehalose, D-xylose, and sorbitol.

In some embodiments wherein an acidic compound is the first detectable product, the first differential indicator system further can comprise a pH indicator. A number of pH indicators to detect acidic compounds produced by bacteria are known in the art. Non-limiting examples of suitable pH indicators include phenol red, chlorophenol red, neutral red, bromthymol blue, and bromthymol purple. In some embodiments wherein the first detectable product comprises a gas, the gas may be detected, for example, by trapping the gas (e.g., by trapping the gas in a Durham tube in a broth culture, by trapping the gas in a hydrogel in a thin film culture device, as described in the Interpretation Guide for the PETRIFILM Enterobacteriaceae Count Plate, which is incorporated herein by reference in its entirety).

In some embodiments, the first indicator compound may comprise an enzyme substrate. Suitable a chromogenic or fluorogenic enzyme substrate that is converted (e.g., hydrolyzed by an enzyme) to a first detectable product (e.g. a colored product or a fluorescent product) by a member of a group of *Salmonella* microorganisms that includes a microorganism of the species *Salmonella bongori*. Preferably, the enzyme substrate is converted to the first detectable product by a *Salmonella* microorganism belonging to a species other than *S. bongori* (e.g., *S. enterica*). Nonlimiting examples of suitable enzyme substrates include enzyme substrates to detect caprylate esterase enzyme activity or to detect α-galactosidase enzyme activity. Suitable chromogenic enzyme substrates include, for example, an enzyme substrate selected from the group consisting of 5-bromo-6-chloro-3-indolyl caprylate, 4-nitrophenyl caprylate, 2-naphthyl caprylate, 5-bromo-4-chloro-3-indoxyl-α-D-galactopyranoside, resorufinyl-α-D-galactopyranoside, 4-nitrophenyl-α-D-galactopyranoside, and combinations thereof.

Second differential indicator systems of the present disclosure comprise a second differential indicator compound that can be converted to a second detectable product by a β-galactosidase enzyme activity. Accordingly, the second differential indicator system distinguishes between microorganisms that produce β-galactosidase enzyme activity and microorganisms that do not produce β-galactosidase enzyme activity. For example, many Salmonellae do not produce β-galactosidase enzyme activity and can be differentiated from the lactose-utilizing members of the Enterobacteriaceae family by using an indicator of β-galactosidase enzyme activity, as disclosed by A. Rambach ("New plate medium for facilitated differentiation of *Salmonella* spp. From *Proteus* spp. And other enteric bacteria", 1990, Appl. Environ. Microbiol., vol. 56, pp. 301-303; which is incorporated herein by reference in its entirety).

However, some reports indicate greater than 90% of the isolated microorganisms from some *Salmonella* species (e.g., *S. bongori*) and subspecies (e.g., *S. enterica arizonae* and *S. enterica diarizonae*) have been found to produce β-galactosidase enzyme activity (for example, see A. M. Littell, "Plating medium for differentiating *Salmonella arizonae* from other Salmonellae", 1977, Appl. Environ. Microbiol., vol. 33, pp. 485-487; which is incorporated herein by reference in its entirety). Thus, a culture medium and corresponding procedure designed to distinguish between *Salmonella* microorganisms and non-*Salmonella* microorganisms on the basis of β-galactosidase enzyme activity may erroneously underestimate the number of *Salmonella* microorganisms in a sample if β-galactosidase-producing Salmonellae are present in the sample. The investigators have discovered a method that, surprisingly, is able to distinguish some β-galactosidase-producing *Salmonella* microorganism even when the culture medium used in the method relies on an indicator of β-galactosidase enzyme activity to distinguish between *Salmonella* microorganisms and non-*Salmonella* microorganisms. A non-limiting example of a suitable second differential indicator compound according to the present disclosure is 5-bromo-4-chloro-3-indolyl-β-D-galactopyranoside, 5-bromo-3-indolyl-β-D-galactopyranoside, 5-bromo-6-chloro-3-indolyl-β-D-galactopyranoside, 2-nitrophenyl-β-D-galactopyranoside, 4-nitrophenyl-β-D-galactopyranoside. In some embodiments, the second differential indicator system comprises lactose and a pH indicator.

Methods of the present disclosure use a first selective agent to inhibit the growth of Gram-positive microorganisms, thereby reducing the competition for nutrients and facilitating the growth of Gram-negative microorganisms such as members of the genus *Salmonella*. Non-limiting examples of suitable first selective agents include a selective agent selected from the group consisting of an antibiotic, bile salts, bile salts No. 3, cholic acid, deoxycholic acid, crystal violet, novobiocin, or a combination of any two or more of the foregoing selective agents.

Methods of the present disclosure optionally may use at least one second selective agent to inhibit the growth of at least one-Gram negative enteric microorganism that is not a member of the genus *Salmonella*. In some embodiments, the second selective agent may also inhibit the growth of at least one Gram-positive microorganism. Advantageously, the second selective agent, in combination with the first selective agent, further inhibits microorganisms (Gram-negative and/or Gram-positive microorganism), thereby reducing the competition for nutrients and facilitating the growth of a *Salmonella* microorganism. In addition, the at least one second selective agent may also substantially prevent the growth of a non-*Salmonella* Gram-negative microorganism that otherwise would convert the first differential compound and/or third differential compound to its respective detectable product. Thus, the second selective agent may reduce the probability of a non-*Salmonella* microorganism being interpreted as a possible *Salmonella* microorganism. Non-limiting examples of suitable second selective agents include a selective agent selected from the group consisting of a β-lactam antibiotic, an aminoglycoside antibiotic, a quinolone antibiotic, a sulfa antibiotic, a polymyxin antibiotic, and a combination of any two or more of the foregoing antibiotics. In one embodiment, the at least one second selective agent comprises a combination of naladixic acid, streptomycin, and polymyxin B. Preferably, the concentration of each of the at least one second selective agents in the nutrient medium is selected to permit the growth of a *Salmonella* microorganism. More preferably, the concentration of each of the at least one second selective agents in the nutrient medium is selected to permit the growth of all *Salmonella* microorganisms.

Methods of the present disclosure comprise contacting, in the culture device, the nutrient medium, the first selective agent, the first differential indicator system, and the second differential indicator system with a sample to form an inoculated culture medium. The sample can be brought into contact in the culture device with the nutrient medium, the first selective agent, the first differential indicator system, and the second differential indicator system in any of a variety of ways. For example, in one embodiment of the method, the nutrient medium, the first selective agent, the first differential indicator system, and the second differential indicator system can be placed into the culture device as a mixture in a hydrated form (e.g., in a hydrated agar culture medium, for example). In this embodiment, the sample (e.g., a liquid sample, a solid sample, a liquid and/or solid sample captured on a filter, a solid sample suspended in a liquid medium) can be deposited and, optionally distributed, into or onto the mixture by techniques that are known in the art such as, for example, pipetting, spread plate inoculation techniques, and streak plate inoculation techniques.

In an alternative embodiment, the sample (e.g., comprising a liquid and/or solid material) is brought into contact and mixed with a liquid mixture (e.g., a molten, tempered liquid agar solution) comprising the nutrient medium, the first selective agent, the first differential indicator system, and the second differential indicator system and subsequently the mixture is transferred to the culture device.

In another alternative embodiment, one or more of the components (e.g., the nutrient medium, the first selective agent, the first differential indicator system, and the second differential indicator system) may be disposed in a culture device a dehydrated form such as in a thin film culture device similar to the culture devices disclosed in U.S. Pat. Nos. 4,565,783; 5,601,998; 5,681,712; 6,265,203; and 6,638,755. In this embodiment, the sample (e.g., an aqueous liquid sample or a solid sample suspended in an aqueous suspending medium) can be brought into contact with the dehydrated components by pipetting the sample into the culture device, for example. In this embodiment, one or more of the components may be dissolved or suspended in the sample before or after the sample is deposited into the culture device.

In yet another alternative embodiment, one or more of the components (e.g., the nutrient medium, the first selective agent, the first differential indicator system, and the second differential indicator system) may be disposed in a culture device a dehydrated form such as in a thin film culture device, as described herein. A suitable aqueous liquid (e.g., sterile water, a sterile buffer; optionally comprising one or more of the components) is pipetted into the culture device and the gelling agent, if present, in the culture device is allowed to rehydrate. Subsequently, the sample can be deposited (e.g., by pipetting, streaking, placement of a membrane filter comprising the sample) into the culture device in contact with the components.

A person having ordinary skill in the art will recognize a variety of other procedures in which the components (e.g., the nutrient medium, the first selective agent, the first differential indicator system, and the second differential indicator system) can be brought into contact with the sample in a culture device.

Methods of the present disclosure further comprise incubating the inoculated culture device for a first period of time. Incubating the inoculated culture device can comprise holding the device at an elevated temperature (e.g., in a temperature-controlled incubator). Incubating the inoculated culture device at an elevated temperature (e.g., greater than 25 degrees C.) facilitates the growth of enteric microorganisms such as microorganisms of the genus *Salmonella*. Most techniques for culturing *Salmonella* microorganism involve placing the culture device in an environment of about 37 degrees C. (approximately the body temperature of a human) However, at this temperature, members of the species *Salmonella bongori* are capable of producing β-D-galactosidase enzyme activity that is detectable using the second differential indicator system of the present disclosure. However, many of the *Salmonella bongori* are able to grow, but do not produce β-D-galactosidase enzyme activity that is detectable using the second differential indicator system of the present disclosure, at temperatures greater than 40 degrees C. Thus, methods of the present disclosure comprise incubating the inoculated culture device at a temperature greater than 40 degrees C. (e.g., at temperatures greater than or equal to 41 degrees C.) for a first period of time. In some embodiments, incubating the inoculated culture device comprises incubating the inoculated culture device at a temperature between 41 degrees C. and 44 degrees C., inclusive. In some embodiments, incubating the inoculated culture device comprises incubating the inoculated culture device at a temperature at 41 degrees C. In some embodiments, incubating the inoculated culture device comprises incubating the inoculated culture device at a temperature at 42 degrees C. In some embodiments, incubating the inoculated culture device comprises incubating the inoculated culture device at a temperature at 43 degrees C. In some embodiments, incubating the inoculated culture device comprises incubating the inoculated culture device at a temperature at 44 degrees C.

The culture device is incubated for a first period of time sufficient to permit the growth and multiplication of enteric microorganisms present in the sample. Typically, the culture device will be incubated for a first period of about 10 hours. In some embodiments, the culture devices are incubated for a first period of about 14 to about 48 hours. In some embodiments, the culture devices are incubated for a first period of about 18 to about 48 hours. In some embodiments, the culture devices are incubated for a first period of about 24 to about 36 hours. In a preferred embodiment, the culture devices are incubated for a period of about 24±2 hours.

Methods of the present disclosure include observing the culture device to detect a presence or an absence of the first detectable product. The first detectable product is produced by a member of a group of *Salmonella* microorganisms that includes a microorganism of the species *Salmonella bongori*. The member of the group converts the first differential indicator compound (e.g., via fermentation, via metabolic activity, via an enzyme activity) to the first detectable product. Typically, the nutrient medium is observed after the first incubation period. In any embodiment, observing the nutrient medium to detect the presence of the first detectable product can comprise observing the culture device to detect a first detectable color. In some embodiments, the first detectable color can be detected by fluorescence (e.g., in an embodiment wherein the first differential indicator compound comprises 4-methylumbelliferyl-α-D-galactopyranoside).

In an embodiment wherein the first differential indicator system comprises a fermentable carbohydrate and a pH indicator, the first detectable color may be a colored zone associated with the pH indicator proximate (i.e., adjacent) a colony of microorganisms capable of converting the carbohydrate to one or more acidic products. Thus, as the acid products accumulate in the colony and/or the nutrient medium surrounding the colony, a colored zone, resulting from the interaction of the acidic products with the pH indicator, forms proximate the colony and, in some instances, may also color the colony. The size of said acid zone may be controlled by the use of a buffer in the nutrient medium, as described in U.S. Pat. No. 5,601,998.

In an embodiment wherein the first differential indicator compound comprises a chromogenic enzyme substrate, the first detectable color may be a colored zone proximate a microorganism colony. For example, the colored zone may comprise a water-soluble product (e.g., 4-nitrophenol) resulting from a microbial enzyme reacting with the chromogenic substrate (e.g., 4-nitrophenyl-α-D-galactopyranoside). Alternatively, the colored zone may comprise a water-insoluble product (e.g., indigo) resulting from a microbial enzyme reacting with the chromogenic substrate (5-bromo-4-chloro-3-indolyl-α-D-galactopyranoside).

Methods of the present disclosure include observing the culture device to detect a presence or an absence of the second detectable product. The second detectable product is produced by a microorganism having β-galactosidase enzyme activity. The microorganism having β-galactosidase enzyme activity converts the second differential indicator compound to the second detectable product. Typically, the nutrient medium is observed after the first incubation period. In any embodiment, observing the nutrient medium to detect the presence of the second detectable product can comprise observing the culture device to detect a second detectable color. In some embodiments, the second detectable color can be detected by observing the absorbance or reflectance of light. In some embodiments, the second detectable color can be detected by fluorescence (e.g., in an embodiment wherein the first differential indicator compound comprises 4-methylumbelliferyl-β-D-galactopyranoside).

A person having ordinary skill in the art will recognize that, in any embodiment, the first detectable product should not substantially interfere with the detection (e.g., by color masking or fluorescent quenching) of the second detectable product and the second detectable product should not substantially interfere with the detection (e.g., by color masking or fluorescent quenching) of the first detectable product. A person having ordinary skill in the art will recognize that, in an embodiment wherein the first detectable color and the second detectable color are detected by fluorescence, the first detectable product should comprise a different fluorophore than the second detectable product.

Methods of the present disclosure include observing the culture device to detect a first detectable product and/or a second detectable product. In any embodiment of the method, observing the culture device can comprise observing the mixture comprising the nutrient medium; the first selective agent; the first differential indicator system; the second selective ingredient; the second selective agent, if present; and the third differential indicator system, if present. In any embodiment of the method, observing the culture device can comprise observing the culture device visually (e.g., using one or more human eyes).

Additionally or alternatively, in any embodiment of the method, observing the culture device can comprise observing the culture device mechanically (e.g., using an imaging system such as, for example, the imaging system described in U.S. Pat. Nos. 6,243,486; 7,496,225; and 7,351,574; each of which is incorporated herein by reference in its entirety. In this embodiment, observing the culture device can comprise creating an image of the culture device using an imaging device. In addition to creating an image of the culture device, the method optionally can comprise analyzing the image using a processor.

Methods of the present disclosure can be used to detect and, optionally, enumerate *Salmonella* microorganisms in a sample. For example, observing the presence of the first detectable product in the culture device can indicate a possible presence, in the sample, of a *Salmonella* microorganism (e.g., a member of the species *Salmonella bongori* and/or a member of the species *Salmonella enterica*). However, in methods according to the present disclosure, observing the presence of the first detectable product juxtaposed with the second detectable product indicates a presence, in the sample, of a microorganism other than a β-galactosidase-producing member of the species *Salmonella bongori*.

The third differential indicator compound can be any suitable indicator compound to detect a *Salmonella* microorganism, provided the third detectable product derived therefrom is distinguishable; preferably, optically distinguishable, more preferably, visually distinguishable; from the first detectable product of the first differential indicator system and the second detectable product of the second differential indicator system. Thus, in one embodiment, the third differential indicator system may comprise a pH indicator in conjunction with a nutrient (e.g., a carbohydrate) that can be converted (e.g., via fermentation) to a first detectable product (e.g., an acidic compound such as lactic acid, for example, and/or a gas such as carbon dioxide, for example), as described herein. In another embodiment, the third differential indicator system may comprise a chromogenic enzyme substrate, as described herein. In yet another embodiment, the third differential indicator system may be a chromogenic enzyme substrate, as described herein. Any first differential indicator system described herein may be suitable for use as a third differential indicator system, provided it does not substantially interfere with, and is distinguishable from, the first and second differential indicator systems and/or the fourth indicator system, if present.

Advantageously, the third differential indicator system can be used as a means to "confirm" the presence of a *Salmonella* microorganism in the sample. That is, when a presence of a first detectable product is observed in the culture device, that presence can be inferred as an indication of the possible presence of a *Salmonella* microorganism in the sample. However, when a presence of a third detectable product is observed in juxtaposition with the presence of the first detectable product (i.e., the first and third detectable products are associated with the same bacterial colony); the observation can indicate a higher likelihood (e.g., a significantly higher likelihood) of the presence of a *Salmonella* microorganism in the sample.

Incubating the inoculated culture device for a second period of time can comprise holding the device at an elevated temperature (e.g., in a temperature-controlled incubator). Incubating the inoculated culture device at an elevated temperature (e.g., greater than 25 degrees C. but less than or equal to about 44 degrees C.) can facilitate the conversion by enteric microorganisms (e.g., members of the genus *Salmonella*) of the third differential indicator compound to the third detectable product. In a preferred embodiment, the culture device will be incubated for a second period of time at a temperature between 35 to 42 degrees C., inclusive. In a more preferred embodiment, the culture device will be incubated for a second period of time at a temperature between 42 degrees C.±1 degree C.

In some embodiments, the third differential indicator system is contacted with the inoculated nutrient medium after the first period of incubation. Advantageously, this may reduce the length of the second incubation period necessary to detect the third detectable product. Thus, in some embodiments, the second incubation period can be 1 hour to about 6 hours. In some embodiments, the second incubation period can be about 2 hours to about 4 hours. In a preferred embodiment, the second incubation period is 4 hours±1 hour.

Figure 2:
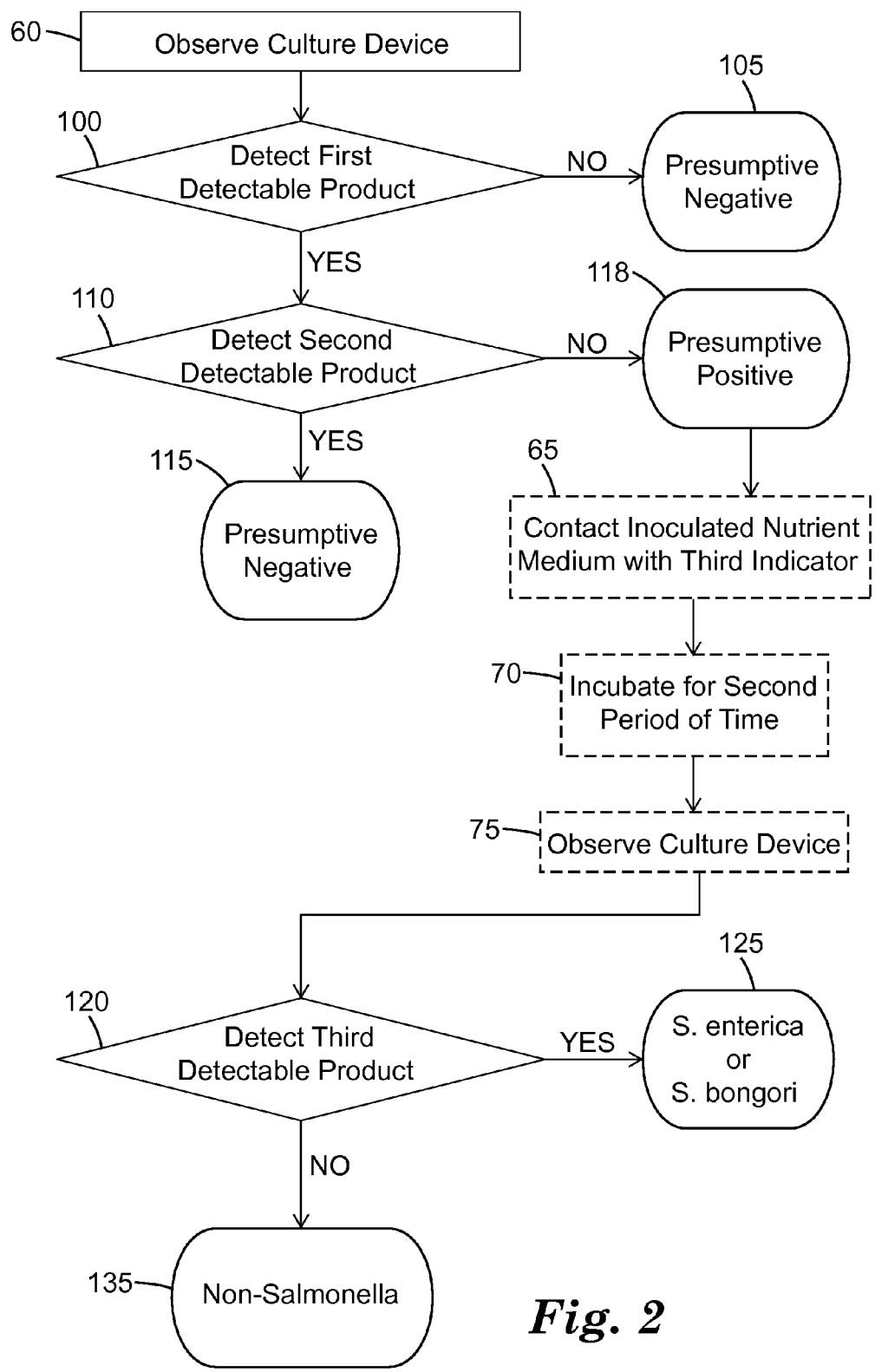
FIG. 2 shows a block diagram of additional analytical steps and optional process steps associated an embodiment of the method shown in FIG. 1.

When used according to the present disclosure, the method can detect the presence or absence of a *Salmonella* microorganism in a sample. FIG. 2 shows one embodiment of several analytical steps and optional process steps associated with the method shown in FIG. 1. After the culture device is incubated for a first period of time, as shown in FIG. 1, the culture device is observed (step 60) to detect (step 100) a presence or an absence of a first detectable product and to detect (step 110) a presence or an absence of a second detectable product. The first and/or second detectable products can be detected as described herein.

If the first detectable product is not detected after a sufficient period of incubation, the test sample is presumed not to contain a *Salmonella* microorganism, as shown in step 105. If the first detectable product is observed, the culture device further is observed (step 110) for the presence of the second detectable product juxtaposed with the first detectable product. If the first detectable product is observed juxtaposed the second detectable product, the sample is presumed not to contain a *Salmonella* microorganism, as shown in step 115.

If the first detectable product is observed to be associated with a microbial colony and the second detectable product is not observed, or if the second detectable product is not juxtaposed with the first detectable product proximate the microbial colony, the test sample is presumed to contain at least one *Salmonella* microorganism, as shown in step 118. The *Salmonella* microorganism may be a member of the species *S. bongori* or it may be a non-β-galactosidase-producing member of the species *S. enterica*. Optionally, the operator may want to confirm whether a microorganism producing the first detectable product is a member of the genus *Salmonella*. This can be accomplished, for example, by performing the optional step 65 of contacting the inoculated nutrient medium with the third indicator system (e.g., by providing an article comprising the third indicator system and contacting the inoculated nutrient medium with the article), as disclosed herein. The optional contacting step 65 is followed by the optional step 70 of incubating the inoculated culture device for a second period of time, as described herein. After the second incubation period, the culture device is observed (step 75) to detect (step 120) a presence or an absence of a third detectable product, as described herein. If the third detectable product is observed, it can be concluded that the microbial colony having the first and third detectable products associated therewith is likely a member (e.g., an α-galactosidase-producing member) of the genus *Salmonella*, as shown in step 125. If the microorganism colony does not produce the third detectable product, it is presumed the colony is not a member of the genus *Salmonella* (e.g., it may be a non-β-galactosidase-producing enteric microorganism), as shown in step 135.

In any embodiment, the method may further comprise enumerating a number of colonies formed by microorganisms belonging to a group (e.g., a group consisting of *Salmonella* microorganisms, a group consisting of β-galactosidase-producing microorganisms, a group consisting of β-galactosidase-producing *Salmonella*, a group of non-β-galactosidase-producing *Salmonella*). The enumeration may be done simply by counting the number of separate microbial colonies in the culture device according to the indicator system or indicator systems with which each colony reacts.

EMBODIMENTS

Embodiment 1 is a method of detecting *Salmonella* microorganisms, the method comprising:
providing,
a sample to be tested;
a culture device;
a nutrient medium that facilitates growth of a Gram-negative enteric microorganism;
a first selective agent that inhibits the growth of Gram-positive microorganisms;
a first differential indicator system comprising a first differential indicator compound that can be converted to a first detectable product by a member of a group of *Salmonella* microorganisms that includes a microorganism of the species *Salmonella bongori*; and
a second differential indicator system comprising a second differential indicator compound that can be converted to a second detectable product by a β-galactosidase enzyme activity;
contacting in the culture device the nutrient medium, the first selective agent, the first differential indicator system, and the second differential indicator system with a sample to form an inoculated culture device;
incubating the inoculated culture device for a first period of time at a temperature greater than 40 degrees C.;
observing the culture device to detect a presence or an absence of the first detectable product; and
observing the culture device to detect a presence or an absence of the second detectable product;
wherein observing the presence of the first detectable product indicates a possible presence in the sample of a *Salmonella* microorganism;
wherein observing the presence of the first detectable product juxtaposed with the second detectable product indicates a presence in the sample of a microorganism other than a β-galactosidase-producing member of the species *Salmonella bongori*.

Embodiment 2 is the method of Embodiment 1, wherein the culture device is provided as a thin film culture device with the nutrient medium, the first selective agent, the first differential indicator system, and the second differential indicator system disposed therein in a substantially dehydrated form.

Embodiment 3 is the method of Embodiment 1 or Embodiment 2, wherein observing the absence of the first detectable product indicates an absence of a *Salmonella* microorganism in the sample.

Embodiment 4 is the method of any one of the preceding Embodiments, wherein observing the nutrient medium to detect the presence of the first detectable product comprises observing the culture device to detect a first detectable color.

Embodiment 5 is the method of any one of the preceding Embodiments, wherein the first differential indicator compound comprises an enzyme substrate.

Embodiment 6 is the method of Embodiment 5, wherein the enzyme substrate comprises an enzyme substrate to detect caprylate esterase enzyme activity or to detect α-galactosidase enzyme activity.

Embodiment 7 is the method of Embodiment 6, wherein the enzyme substrate is selected from the group consisting of 5-bromo-6-chloro-3-indolyl caprylate, 4-nitrophenyl caprylate, 2-naphthyl caprylate, 5-bromo-4-chloro-3-indoxyl-α-D-galactopyranoside, resorufinyl-α-D-galactopyranoside, and 4-nitrophenyl-α-D-galactopyranoside.

Embodiment 8 is the method of any one of Embodiments 5 through 7, wherein the first detectable product is substantially water-insoluble.

Embodiment 9 is the method of any one of Embodiments 1 through 6, wherein the first differential indicator system comprises a pH indicator and at least one carbohydrate selected from the group consisting of melibiose, 2-deoxy-D-ribose, mannitol, L-arabinose, dulcitol, maltose, L-rhamnose, trehalose, D-xylose, and sorbitol.

Embodiment 10 is the method of any one of the preceding Embodiments, wherein the first detectable product is substantially water-soluble, wherein observing the first detectable product comprises observing a colored zone adjacent a microbial colony.

Embodiment 11 is the method of any one of the preceding Embodiments, wherein observing the second detectable product comprises observing the culture device to detect a second detectable color.

Embodiment 12 is the method of any one of the preceding Embodiments, wherein the second differential indicator compound is selected from the group consisting of 5-bromo-4-chloro-3-indolyl-β-D-galactopyranoside, 5-bromo-3-indolyl-β-D-galactopyranoside, 5-bromo-6-chloro-3-indolyl-β-D-galactopyranoside, 2-nitrophenyl-β-D-galactopyranoside, and 4-nitrophenyl-β-D-galactopyranoside.

Embodiment 13 is the method of any one of the preceding Embodiments, wherein the first detectable product is substantially water-soluble and the second detectable produce is substantially water-insoluble or, alternatively, wherein the first detectable product is substantially water-insoluble and the second detectable produce is substantially water-soluble.

Embodiment 14 is the method of any one of Embodiments 1 through 13, wherein the first selective agent is selected from the group consisting of an antibiotic, bile salts, bile salts No. 3, deoxycholic acid, cholic acid, deoxycholic acid, crystal violet, novobiocin, nalidixic acid, polymyxin B, streptomycin, methicillin, cefsoludin, or a combination of any two or more of the foregoing selective agents.

Embodiment 15 is the method of any one of the preceding Embodiments, wherein the culture device further comprises at least one second selective agent, wherein the at least one second selective agent inhibits the growth of at least one Gram-negative enteric microorganism that is not a member of the genus *Salmonella*.

Embodiment 16 is the method of Embodiment 15, wherein the second selective agent is selected from the group consisting of a β-lactam antibiotic, an aminoglycoside antibiotic, a quinolone antibiotic, a sulfa antibiotic, a polymyxin antibiotic, and a combination of any two or more of the foregoing antibiotics.

Embodiment 17 is the method of Embodiment 16, wherein the at least one second selective agent comprises a combination of naladixic acid, streptomycin, and polymyxin B.

Embodiment 18 is the method of any one of the preceding Embodiments, wherein incubating the culture device comprises incubating the culture device at a temperature between 41-44 degrees C., inclusive.

Embodiment 19 is the method of any one of the preceding Embodiments, further comprising:

providing an article with a third differential indicator system comprising a third differential indicator compound that can be converted by a *Salmonella* microorganism to a third detectable product;

contacting the article with the inoculated culture device;

incubating the inoculated culture device for a second period of time; and observing the culture device to detect the third detectable product;

wherein observing the third detectable product juxtaposed with the first detectable product indicates the presence of a *Salmonella* microorganism in the sample.

Embodiment 20 is the method of any one of the preceding Embodiments, further comprising:

providing a nondifferential indicator compound that can be converted by an enteric microorganism to a fourth detectable product; and observing the culture device to detect a presence or an absence of the fourth detectable product;

wherein contacting in the culture device the nutrient medium, the first selective agent, the first differential indicator system, and the second differential indicator system with a sample to form an inoculated culture device further comprises contacting in the culture device the nutrient medium, the first selective agent, the first differential indicator system, the second differential indicator system, and the nondifferential indicator compound with the sample to form the inoculated culture device.

Embodiment 21 is the method of any one of the preceding Embodiments, wherein observing the culture device comprises observing the culture device visually.

Embodiment 22 is the method of any one of the preceding Embodiments, wherein observing the culture device comprises creating an image of the culture device using an imaging device.

Embodiment 23 is the method of Embodiment 22, further comprising analyzing the image using a processor.

Embodiment 24 is the method of any one of the preceding Embodiments, further comprising enumerating a number of colonies formed by microorganisms belonging to the group.

EXAMPLES

Objects and advantages of this invention are further illustrated by the following examples, but the particular materials and amounts thereof recited in these examples, as well as other conditions and details, should not be construed to unduly limit this invention. Unless otherwise indicated, all parts and percentages are on a weight basis, all water is distilled water, and all molecular weights are weight average molecular weight.

Materials.

Materials utilized in the preparation of the examples are shown in Table 1.

TABLE 1

Materials

| Component | Description | Source |
|---|---|---|
| TSA | tryptic soy agar | |
| Buffered peptone water | | EMD Chemicals, Inc., Gibbstown, NJ |
| Butterfield's Buffer | | Edge Biologicals, Inc.; Memphis, TN |

TABLE 1-continued

Materials

| Component | Description | Source |
|---|---|---|
| Tris | -- Tris (2-Amino-2-hydroxymethyl-propane-1,3-diol) | Sigma Chemical Co.; St. Louis, MO |
| TSA Slant | Tryptic Soy Agar Slant | VWR International, Radnor, PA |
| X-gal | 5-Bromo-4-Chloro-3-Indoxyl-β-D-galactopyranoside | Biosynth AG; Staad, Switzerland |
| IPTG | isopropyl-β-D-thiogalactopyranoside | Sigma-Aldrich; St. Louis, MO |
| Streptomycin sulfate salt | | Sigma-Aldrich |
| Polymyxin B sulfate salt | | Sigma-Aldrich |
| Nalidixic acid sodium salt | | Sigma-Aldrich |

Bacterial strains used in the Examples are listed in Table 2. Bacterial strains with a designation of "FSD" followed by a number were isolated from a food sample or from a food-processing environment. The identity of *S. agona* FSD122 was confirmed by DNA sequence analysis. Bacterial strains with a designation of "ATCC" followed by a number were obtained from the American Type Culture Collection, Manassas, Va.

TABLE 2

Bacterial Strain List

| Strain Designation | Identity |
|---|---|
| ATCC43975 | Salmonella bongori |
| FSD122 | Salmonella bongori |
| FSD2577 | Salmonella bongori |
| FSD2579 | Salmonella bongori |
| FSD140 | Salmonella enterica serovar agona |
| FSD99001 | Salmonella enterica subsp. arizonae |
| FSD17 | Salmonella enterica subsp. arizonae |
| FSD115 | Salmonella enterica subsp. arizonae |
| FSD43973 | Salmonella enterica subsp. diarizonae |
| FSD99002 | Citrobacter freundii |
| ATCC25922 | Escherichia coli |

Example 1. Preparation of a *Salmonella* Thin Film Culture Device

A thin film culture device was prepared according to the procedure described in International Publication No. WO2012/161992, which is incorporated herein by reference in its entirety. The powder composition used to prepared the powder-coated paper substrate was made by mixing 2 parts by weight of 2-deoxy-D-ribose (2DDR; Research Products International Corp.; Mt. Prospect, Ill.) and 98 parts of guar gum (M150 guar MEYPROGAT gum, Meyhall Chemical AG). Before powder-coating, the paper was coated with the adhesive containing TTC.

The broth coating mixture was prepared by adding the materials listed in Table 3 to 1 liter of deionized water in a container, and was mixed according to the method described in Example 1 of U.S. Pat. No. 6,022,682.

TABLE 3

Ingredients for broth coating mixture.

| Material | Amount (grams) |
|---|---|
| Proteose Peptone No. 3 | 50.0 |
| Porcine Peptone | 14.0 |
| Yeast Extract | 6.0 |
| Sodium Chloride | 10.0 |
| MOPS acid | 3.2 |
| MOPS sodium salt | 5.2 |
| Phenol Red sodium salt | 1.0 |
| Bile Salt No. 3 | 2.0 |
| 5-Bromo-4-Chloro-3-Indoxyl-β-D-galactopyranoside | 0.8 |
| Guar | 14 |

A selective agent mixture was prepared by adding 0.1 g of IPTG, 2.0 g urea, 5.0 g Melibiose (Sigma), 0.005 g Nalidixic acid sodium salt, 0.005 g Streptomycin sulfate salt and 0.00075 g Polymyxin B sulfate salt to 30 ml of sterile deionized water in a 50 mL sterile centrifuge tube and vortexed to mix. The broth mixture was cooled to about 40° C. and the selective agent mixture was added with vigorous mixing. A cover film was prepared by coating the broth onto the corona-treated side of a 2.9 mil polyester film.

The culture device was assembled according to U.S. Pat. No. 6,022,682; with the base member, a foam spacer having a 7.3 cm diameter circle cut from the center to provide a well, and the cover plate adhered together using an adhesive transfer tape. The plates measured approximately 10.3 cm by 10.2 cm with a circular well exposing the dried broth-coated mixture at about the center of the plate.

Example 2. Effect of Incubation Temperature on β-Galactosidase Activity Produced by Various Strains of Enterobacteriaceae Culture devices were made according to Example 1. The growth medium in each culture device was hydrated with 1 milliliter of sterile Butterfield's buffer before use. The devices were held at room temperature for at least one hour prior to inoculating them in order to permit the hydrogel to swell.

A colony from individual pure cultures (on TSA slants) of each of the strains listed in Table 2 was transferred to individual sterile vials containing 1.0 mL of buffered peptone water and incubated at 37° C. for 24±2 hours to produce a pure bacterial suspension of each strain. The *Salmonella* suspensions were each diluted 1:100 in Butterfield's buffer. The *E. coli* suspension was not diluted. Each diluted and undiluted suspension was then inoculated onto a by streaking with a 10 microliter sterile plastic loop. A set of inoculated culture devices, each streaked with a different bacterium was prepared in this manner. The set of culture devices was then sealed in a plastic bag and incubated by immersing in a water bath. Bags were incubated in this method at the following temperatures: 39° C., 40° C., 41° C., 42° C., 43° C., 44° C. and 45° C. The water bath temperatures were controlled to ±0.1° C. and bags were immersed for 24±2 hours hours. Two replicates of each bacterium were tested. The incubated culture devices were removed from the bags and observations are shown in Table 4.

TABLE 4

Observed results.

| Microorganism | Observations |
| --- | --- |
| S. bongori (ATCC43975) | A blue precipitate was observed adjacent the colonies on plates incubated at 39° C. and 40° C. No blue precipitate was observed adjacent colonies on plates incubated at 41° C., 42° C., 43° C., 44° C., and 45° C. At 45° C., the colonies appeared smaller. |
| S. bongori (FSD122) | A blue precipitate was observed adjacent the colonies when incubated at 39° C. and 40° C. No blue precipitate was observed adjacent colonies when incubated at 41° C., 42° C., 43° C., 44° C., and 45° C. At 45° C., the colonies appeared smaller. |
| S. enterica serovar agona (FSD140) | No blue precipitate was produced adjacent the colonies when incubated at 39° C., 40° C., 41° C., 42° C., 43° C., 44° C., or 45° C. |
| S. enterica subsp. arizonae (FSD99001) | A blue precipitate (proximate the colonies) was produced by colonies when incubated at 37° C. and 42° C. Other temperatures were not tested. |
| E. coli (ATCC25922) | Blue precipitate (proximate the colonies) was produced by colonies when incubated at 39° C., 40° C., 41° C., 42° C., 43° C., 44° C., or 45° C. |
| S. enterica subsp. diarizonae (FSD43973 | Blue precipitate adjacent the colonies when incubated at 39° C., 40° C., 41° C., 42° C., 43° C., 44° C., or 45° C. |
| S. bongori (FSD2579) | A blue precipitate adjacent the colonies when incubated at 37° C. No blue precipitate was produced by colonies when incubated at 42° C. |
| S. bongori (FSD2577) | A blue precipitate adjacent the colonies when incubated at 37° C. No blue precipitate was produced by colonies when incubated at 42° C. |
| S. enterica subsp. arizonae (FSD115) | Blue precipitate adjacent the colonies when incubated at 39° C., 40° C., 41° C., 42° C., 43° C., 44° C., or 45° C. |
| Citrobacter freundii (FSD99002) | Blue precipitate adjacent the colonies when incubated at 39° C., 40° C., 41° C., 42° C., 43° C., 44° C., or 45° C. |
| S. enterica subsp. arizonae (FSD17) | Blue precipitate adjacent the colonies when incubated at 39° C., 40° C., 41° C., 42° C., 43° C., 44° C., or 45° C. |

The results indicate the test strain of *Salmonella enterica* serovar agona did not produce β-galactosidase activity at any temperature from 39° C. to 45° C. The results further indicate the test strains of *E. coli*, *Citrobacter freundii*, *Salmonella enterica* subsp. *arizonae* and *Salmonella enterica* subsp. *diarizonae* all produced β-galactosidase activity at each temperature between 39° C. and 45° C. The results further indicate test strains of *Salmonella bongori* produced β-galactosidase activity at a temperature less than or equal to 40° C., but did not produce β-galactosidase activity at temperatures above 40° C.

Example 3. The Use of a Detection Article with a Differential Indicator to Confirm the Presence of a *Salmonella* Microorganism A detection article (disk) was prepared as described in Example 1 of PCT International Publication No. WO2012/092181; which is incorporated herein by reference in its entirety.

Thin film culture devices (made as described in Example 1) that contained a presumptive positive result (*Salmonella typhimurium* ATCC 14028 and *Salmonella bongori* FSD 122 inoculated into culture devices and incubated as described in Example 2) were opened and a disk was rolled (to minimize air bubbles) onto the gel surface. The plates were closed and were incubated at 42° C. for 4 hours. The disk was analyzed for color a change adjacent the colonies to confirm whether the colonies reacted with the indicator (5-bromo-4-chloro-3-indolyl-α-D-galactopyranoside) present in the detection article. A change in colony color from red or brown to blue or dark blue indicated the presence of a *Salmonella* microorganism in the colonies. The results of the test are shown in Table 5.

TABLE 5

Interpretation of results observed in culture devices.

| Plate # | Bacteria | *Salmonella* ssp. Confirmation Results |
| --- | --- | --- |
| 1 | Salmonella typhimurium (ATCC 14028) | Positive: Red to brown presumptive colony with a yellow zone around the colony changed to blue to dark blue colony |
| 2 | Salmonella bongori (FSD 122) | Positive: Red to brown presumptive colony with a yellow zone around the colony changed to blue to dark blue colony |

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

Various modifications may be made without departing from the spirit and scope of the invention. These and other embodiments are within the scope of the following claims.

The invention claimed is:

1. A method of detecting *Salmonella* microorganisms, the method comprising:

providing,
  a sample to be tested;
  a culture device;
  a nutrient medium that facilitates growth of a Gram-negative enteric microorganism;
  a first selective agent that inhibits the growth of Gram-positive microorganisms;
  a first differential indicator system comprising a first differential indicator compound that can be converted to a first detectable product by a member of a group of *Salmonella* microorganisms that includes a microorganism of the species *Salmonella bongori;*
  a second differential indicator system comprising a second differential indicator compound that can be converted to a second detectable product by a β-galactosidase enzyme activity;
contacting in the culture device the nutrient medium, the first selective agent, the first differential indicator system, and the second differential indicator system with a sample to form an inoculated culture device;
incubating the inoculated culture device for a first period of time at a temperature greater than 40 degrees C.;
observing the culture device to detect a presence or an absence of the first detectable product; and observing the culture device to detect a presence or an absence of the second detectable product;
wherein observing the presence of the first detectable product indicates a presence in the sample of a *Salmonella* microorganism;
wherein observing the presence of the first detectable product juxtaposed with the second detectable product indicates a presence in the sample of a microorganism other than a β-galactosidase-producing member of the species *Salmonella bongori*.

2. The method of claim 1, wherein the culture device is provided as a thin film culture device with the nutrient medium, the first selective agent, the first differential indicator system, and the second differential indicator system disposed therein in a dehydrated form.

3. The method of claim 1, wherein observing the absence of the first detectable product indicates an absence of a *Salmonella* microorganism in the sample.

4. The method of claim 1, wherein observing the nutrient medium to detect the presence of the first detectable product comprises observing the culture device to detect a first detectable color.

5. The method of claim 1, wherein the first differential indicator compound comprises an enzyme substrate.

6. The method of claim 5, wherein the enzyme substrate comprises an enzyme substrate to detect caprylate esterase enzyme activity or to detect α-galactosidase enzyme activity.

7. The method of claim 6, wherein the enzyme substrate is selected from the group consisting of 5-bromo-6-chloro-3-indolyl caprylate, 4-nitrophenyl caprylate, 2-naphthyl caprylate, 5-bromo-4-chloro-3-indoxyl-α-D-galactopyranoside, resorufinyl-α-D-galactopyranoside, and 4-nitrophenyl-α-D-galactopyranoside.

8. The method of claim 5, wherein the first detectable product is water-insoluble.

9. The method of claim 1, wherein the first differential indicator system comprises a pH indicator and at least one carbohydrate selected from the group consisting of melibiose, 2-deoxy-D-ribose, mannitol, L-arabinose, dulcitol, maltose, L-rhamnose, trehalose, D-xylose, and sorbitol.

10. The method of claim 1, wherein the first detectable product is water-soluble, wherein observing the first detectable product comprises observing a colored zone adjacent to a microbial colony.

11. The method of claim 1, wherein observing the second detectable product comprises observing the culture device to detect a second detectable color.

12. The method of claim 1, wherein the second differential indicator compound is selected from the group consisting of 5-bromo-4-chloro-3-indolyl-1-β-D-galactopyranoside, 5-bromo-3-indolyl-β-D-galactopyranoside, 5-bromo-6-chloro-3-indolyl-β-D-galactopyranoside, 2-nitrophenyl-β-D-galactopyranoside, and 4-nitrophenyl-β-D-galactopyranoside.

13. The method of claim 1, wherein the first detectable product is water-soluble and the second detectable produce is water-insoluble or, alternatively, wherein the first detectable product is water-insoluble and the second detectable produce is water-soluble.

14. The method of claim 1, wherein the first selective agent is selected from the group consisting of an antibiotic, bile salts, bile salts No. 3, deoxycholic acid, cholic acid, crystal violet, novobiocin, nalidixic acid, polymyxin B, streptomycin, methicillin, cefsoludin, or a combination of any two or more of the foregoing selective agents.

15. The method of claim 1, wherein the culture device further comprises at least one second selective agent, wherein the at least one second selective agent inhibits the growth of at least one Gram-negative enteric microorganism that is not a member of the genus *Salmonella*.

16. The method of claim 15, wherein the second selective agent is selected from the group consisting of a β-lactam antibiotic, an aminoglycoside antibiotic, a quinolone antibiotic, a sulfa antibiotic, a polymyxin antibiotic, and a combination of any two or more of the foregoing antibiotics.

17. The method of claim 16, wherein the at least one second selective agent comprises a combination of naladixic acid, streptomycin, and polymyxin B.

18. The method of claim 1, wherein incubating the culture device comprises incubating the culture device at a temperature between 41 to 44 degrees C.

19. The method of claim 1, further comprising:
  providing an article with a third differential indicator system comprising a third differential indicator compound that can be converted by a *Salmonella* microorganism to a third detectable product;
  contacting the article with the inoculated culture device;
  incubating the inoculated culture device for a second period of time; and
  observing the culture device to detect the third detectable product;
  wherein observing the third detectable product juxtaposed with the first detectable product indicates the presence of a *Salmonella* microorganism in the sample.

20. The method of claim 19, further comprising:
  providing a nondifferential indicator compound that can be converted by an enteric microorganism to a fourth detectable product; and
  observing the culture device to detect a presence or an absence of the fourth detectable product;
  wherein contacting in the culture device the nutrient medium, the first selective agent, the first differential indicator system, and the second differential indicator system with a sample to form an inoculated culture device further comprises contacting in the culture device the nutrient medium, the first selective agent, the first differential indicator system, the second differential indicator system, and the nondifferential indicator compound with the sample to form the inoculated culture device.

21. The method of claim 1, wherein observing the culture device comprises observing the culture device visually.

22. The method of claim 1, wherein observing the culture device comprises creating an image of the culture device using an imaging device.

23. The method of claim 22, further comprising analyzing the image using a processor.

24. The method of claim 1, further comprising enumerating a number of colonies formed by microorganisms belonging to the group.

25. The method of claim 1, wherein the culture device comprises a gelling agent.

26. The method of claim 1, wherein observing the culture device to detect a presence or an absence of the first detectable product comprises observing the culture device to detect the presence or an absence of the first detectable product proximate a microbial colony, and wherein observing the presence of the first detectable product juxtaposed with the second detectable product comprises observing the presence of the first detectable product proximate the microbial colony.

* * * * *

UNITED STATES PATENT AND TRADEMARK OFFICE
CERTIFICATE OF CORRECTION

PATENT NO. : 9,677,111 B2
APPLICATION NO. : 14/368525
DATED : June 13, 2017
INVENTOR(S) : Christine A. Binsfeld et al.

Page 1 of 1

It is certified that error appears in the above-identified patent and that said Letters Patent is hereby corrected as shown below:

On the Title Page

Item (72), Inventors, "Chirstine" should read --Christine--.
Item (56), References Cited, under OTHER PUBLICATIONS, Line 13, "*Salmonellai*" should read --*Salmonellae*--.

In the Specification

Column 3,
Line 11, "cefsoludin," should read --cefsulodin,--.

Column 9,
Line 22, both occurrences of "bromthymol" should read --bromothymol--.

Column 12,
Line 9, "human)" should read --human).--.

Column 17,
Line 44, "cefsoludin," should read --cefsulodin,--.

Column 19,
Line 46, "*colf*" should read --*coli*--.

In the Claims

Column 24,
Line 24, in Claim 14, "cefsoludin," should read --cefsulodin,--.

Signed and Sealed this
Twenty-seventh Day of March, 2018

Andrei Iancu
*Director of the United States Patent and Trademark Office*